US012394045B2

(12) United States Patent
Wang et al.

(10) Patent No.: US 12,394,045 B2
(45) Date of Patent: Aug. 19, 2025

(54) DEEP LEARNING BASED AUXILIARY DIAGNOSIS SYSTEM FOR EARLY GASTROINTESTINAL CANCER AND INSPECTION DEVICE

(71) Applicant: Guohua Wang, Chongqing (CN)

(72) Inventors: Guohua Wang, Chongqing (CN); Ran Wang, Chongqing (CN); Guoying Bai, Chongqing (CN); Rui Tan, Chongqing (CN)

(73) Assignee: Guohua Wang, Chongqing (CN)

( * ) Notice: Subject to any disclaimer, the term of this patent is extended or adjusted under 35 U.S.C. 154(b) by 684 days.

(21) Appl. No.: 17/678,855

(22) Filed: Feb. 23, 2022

(65) Prior Publication Data

US 2022/0189015 A1 Jun. 16, 2022

Related U.S. Application Data

(63) Continuation of application No. PCT/CN2020/109779, filed on Aug. 18, 2020.

(30) Foreign Application Priority Data

Aug. 23, 2019 (CN) .................. 201910785057.X

(51) Int. Cl.
*G06T 7/00* (2017.01)
*G06V 10/26* (2022.01)
(Continued)

(52) U.S. Cl.
CPC ............ *G06T 7/0012* (2013.01); *G06V 10/26* (2022.01); *G06V 10/7715* (2022.01);
(Continued)

(58) Field of Classification Search
CPC ......... G06T 7/0012; G06T 2207/10068; G06T 2207/30028; G06T 2207/30096;
(Continued)

(56) References Cited

U.S. PATENT DOCUMENTS

2011/0301447 A1 12/2011 Park et al.
2012/0245415 A1 9/2012 Emura et al.
(Continued)

FOREIGN PATENT DOCUMENTS

CN 105013073 11/2015
CN 108695001 10/2018
(Continued)

OTHER PUBLICATIONS

Baldwin et al., "A technical review of flexible endoscopic multi-tasking platforms", International Journal of Surgery, Surgical Assocaites, 10(7), pp. 345-354, May 19, 2012.
(Continued)

*Primary Examiner* — Lewis G West
(74) *Attorney, Agent, or Firm* — Levine Bagade Han LLP

(57) ABSTRACT

A deep learning-based examination and diagnosis assistance system and apparatus for early digestive tract cancer comprising a feature extraction network, an image classification model, an endoscope classifier, and an early cancer recognition model. The feature extraction network is used for performing initial feature extraction on endoscope images based on a neural network model; the image classification model is used for performing extraction on the initial features to acquire image classification features; the endoscope classifier is used for performing feature extraction on the initial features to acquire endoscope classification features and classify gastroscope/colonoscope images; the early cancer recognition model is used for splicing the initial features, the endoscope classification features, and the image classification features to acquire the probability of early cancer lesions in white light images, electronic dye images or chemical dye images of a corresponding site or acquire a flushing prompt or position recognition prompt for the corresponding site.

18 Claims, 7 Drawing Sheets

(51) Int. Cl.
*G06V 10/77* (2022.01)
*G06V 10/80* (2022.01)

(52) U.S. Cl.
CPC .. *G06V 10/806* (2022.01); *G06T 2207/10068* (2013.01); *G06T 2207/30028* (2013.01); *G06T 2207/30096* (2013.01); *G06V 2201/032* (2022.01); *G06V 2201/07* (2022.01)

(58) Field of Classification Search
CPC .. G06V 10/26; G06V 10/7715; G06V 10/806; G06V 2201/032; G06V 2201/07
See application file for complete search history.

(56) References Cited

U.S. PATENT DOCUMENTS

| | | |
|---|---|---|
| 2013/0172680 A1 | 7/2013 | Polyakov et al. |
| 2015/0374210 A1 | 12/2015 | Durr et al. |
| 2016/0037082 A1* | 2/2016 | Wang ..................... H04N 23/90 348/65 |
| 2018/0146845 A1 | 5/2018 | Futatsugi et al. |
| 2018/0153534 A1 | 6/2018 | Lam |
| 2020/0279368 A1* | 9/2020 | Tada .................. A61B 1/00016 |
| 2021/0153808 A1* | 5/2021 | Tada ..................... G06T 7/0016 |
| 2021/0390693 A1 | 12/2021 | Zhang et al. |
| 2024/0320822 A1* | 9/2024 | Kim .......................... G06T 5/73 |

FOREIGN PATENT DOCUMENTS

| | | | |
|---|---|---|---|
| CN | 109118485 | 1/2019 | |
| CN | 109523522 | 3/2019 | |
| CN | 110136106 | 8/2019 | |
| CN | 110211118 | 9/2019 | |
| CN | 110495847 | 11/2019 | |
| JP | 2014527837 | 10/2014 | |
| WO | WO-2015181371 A1 * | 12/2015 | ............ G06T 5/002 |
| WO | WO 2018/225448 | 12/2018 | |

OTHER PUBLICATIONS

Kruk et al., "Recognition and classification of colon cells applying the esemble of classifiers", Computers in Biology and Medicine, 39(2), pp. 156-165, Feb. 2009.

Pacal et al., "A comprehensive review of deep learning in colon cancer", Computers in Biology and Medicine, 126, Sep. 17, 2020.

* cited by examiner

DEEP LEARNING BASED AUXILIARY DIAGNOSIS SYSTEM FOR EARLY GASTROINTESTINAL CANCER AND INSPECTION DEVICE

CROSS-REFERENCE TO RELATED APPLICATIONS

This application is a continuation of International Patent Application Number PCT/CN2020/109779 filed Aug. 18, 2020, which claims the benefit of priority to Chinese Application No. 201910785057.X filed on Aug. 23, 2019, the contents of which are incorporated herein by reference in their entireties.

TECHNICAL FIELD

The present application relates to medical inspection equipment, in particular to a diagnosis assistance system and an inspection device for early digestive tract cancer.

BACKGROUND

With the development of deep learning based artificial intelligence technology, the application of artificial intelligence in the field of medical image diagnosis is gaining more and more attention. Through artificial intelligence technology, possible lesions can be automatically determined based on medical images, and automatic screening of medical images can be achieved. At present, artificial intelligence technology has been widely studied in various fields such as breast cancer pathological inspection, lung cancer detection, and cardiovascular imaging.

Digestive tract diseases are frequently-occurring and common diseases, which seriously threaten human life and health. Digestive endoscopy and chromoendoscopy are the first choices for diagnosing digestive tract diseases. However, the mucosal surface of the digestive tract is often covered with a large amount of foam and mucus, resulting in blurred endoscope vision, seriously affecting an endoscopist's observation, and even causing various false images, which is one of the main reasons for missed diagnosis and misdiagnosis. Therefore, mucosal cleaning during digestive endoscopy is not only one of the main measures to reduce missed diagnosis and misdiagnosis, but also a necessary basis for most mucosal staining.

Routine white light endoscopy for screening digestive tract lesions has a missed diagnosis rate of up to 25%, especially for minimal and flat lesions in the colon. Chromoendoscopy is based on conventional white light endoscopy to stain the mucosa, so that the color contrast between the lesion and the normal mucosa is more obvious, which is helpful for recognition, biopsy and microscopic diagnosis and treatment of the lesion. Chromoendoscopy and other advanced imaging techniques designed to facilitate visualization and detection of tumor lesions have been applied throughout the digestive tract inspection, and chromoendoscopy, especially in combination with magnifying endoscopy, can significantly improve the detection means of digestive tract mucosal tumor lesions.

In China, digestive system tumors have highest incidence among all the tumors, and the incidence of digestive tract tumors such as esophageal cancer, gastric cancer and colorectal cancer ranks among the top six cancer incidence rates in China; especially for gastric cancer, the number of new cases and deaths each year accounts for nearly half of the global number. Studies have found that early detection of digestive tract tumors can greatly improve the cure rate.

Early detection, early diagnosis, and early treatment of digestive tract tumors bring the best results. It is clearly stated in the Chinese Outline of Cancer Prevention and Control that early detection, early diagnosis and early treatment of cancer are the main strategies to reduce mortality and improve survival. On the basis of improving the detection rate and diagnosis rate of early lesions, endoscopic early treatment is an effective way to improve the prognosis of patients with digestive tract tumors, save national medical resources, and reduce the burden on families and society.

Digestive endoscopy and pathological biopsy are the current standards for the detection and diagnosis of early digestive tract cancer in China. A prospective multi-center study on the diagnostic value of four types of enhanced magnifying endoscopy in the screening of early gastric cancer and precancerous lesions, led by Peking Union Medical College Hospital, concluded that pigment magnifying endoscopy is an accurate, simple, safe and affordable method for the diagnosis of early gastric cancer. The diagnostic efficiency of NBI magnifying endoscopy is not superior to that of a pigment magnifying endoscopy.

At present, in realizing the screening of early digestive tract cancer by digestive endoscopy in China, the following major problems still need to be addressed: the tiredness of doctors caused by the great number of inspections in large hospitals; the very unsaturated work of doctors caused by the small number of inspections in small hospitals; the slow improvement of the diagnostic level caused by long training period of doctors; the blurred field of vision often encountered during the inspection, the lack of cleaning means, resulting in time-consuming and ineffective; the incompleteness of staining solutions used for pigment endoscopy, the wide variation in doctor homemade methods, the lack of uniformity in the concentrations used, the wide variation in the methods used, and the inability to form a standardized diagnostic atlas.

SUMMARY

(I) Technical Problems to be Solved

In order to solve the above-mentioned problems in the prior art, the present application provides a diagnosis assistance system and an inspection device for early digestive tract cancer.

(II) Technical Solutions

According to an aspect of the present application, provided is a deep learning based inspection and diagnosis assistance system for early digestive tract cancer, including a feature extraction network, an image classification model, an endoscopic classifier and an early cancer recognition model; wherein the feature extraction network is configured to extract a preliminary feature from an endoscopic image according to a neural network model; the image classification model is configured to perform a second extraction on the preliminary features and acquire image classification features; the endoscopic classifier is configured to extract preliminary features to obtain endoscope classification features and classify gastroscopic or colonoscopy images; the early cancer recognition model is configured to stitch the preliminary features, the endoscope classification features and the image classification features, and obtain a probability of early cancer lesions in a white light image, an electronic staining images or a chemical staining images of a corresponding part or obtain a washing prompt or a position recognition prompt of the corresponding part.

According to another aspect of the present application, provided is a deep learning based inspection and diagnosis assistance device for early digestive tract cancer, including an AI display, an AI processor, a functional module and a control switch; the functional module is a rinsing and staining operation module; wherein, the AI processor is connected with the functional module through an electrical signal line, and is configured to control, according to a judgment result of the AI processor, the functional module based on a signal of the control switch; the functional module and a gastrointestinal endoscope are connected with each other through a rising pipeline and a staining pipeline; and the functional module and the control switch are connected with each other through a line of a foot switch.

(III) Beneficial Effects

Compared with the prior art, on the basis of following the clinical guidelines or expert consensus on screening for early digestive tract cancer, the present application provides an inspection device and system that is suitable for primary medical institutions and most existing gastroscopies, which can guide and supervise doctors as well as improve the level and efficiency of inspection and diagnosis. The device of the present application includes AI-assisted digestive endoscopy, digestive endoscopy quality control and digestive endoscopy diagnostic functions, which can not only guide and urge grassroots doctors to perform digestive endoscopy inspections, but also improve their inspection and diagnosis level. The system and device can be used together with most gastrointestinal endoscope in medical institutions.

The system of the present application combines AI technology with the special mucosal rinsing and cleaning technology and special mucosal staining technology of an AI host, so as to achieve unexpected effects in improving the quality of AI-assisted diagnosis and the diagnostic efficiency of digestive endoscopy.

The mucosal cleaning technology of the system of the present application may improve the sensitivity and specificity of image recognition under the condition of white light endoscopy by providing cleaner and clearer images.

The mucosal staining technology of the system of the present application makes the mucosal staining more comparable by using uniform and standardized production of high-quality staining, which is conducive to forming standardized diagnostic maps, and improves the sensitivity and specificity of image recognition under chromoendoscopy by providing images with better staining effects and greater comparability.

The mucosal cleaning technology of the system of the present application makes the mucosal staining effect better by providing a cleaner and mucus-free mucosa. Through the collaboration of the AI image recognition technology, mucosal cleaning technology and mucosal staining technology of the system of the present application, the efficiency of endoscopy is improved.

BRIEF DESCRIPTION OF THE DRAWINGS

Embodiments of the invention will now be described, by way of example only, with reference to the accompanying drawings in which corresponding reference symbols indicate corresponding parts, and in which.

DETAILED DESCRIPTION

The specific implementations of the present application will be described in further detail below in conjunction with accompanying drawings and embodiments. The following examples are used to illustrate the present application, but not to limit the scope of the present application.

Figure 1:
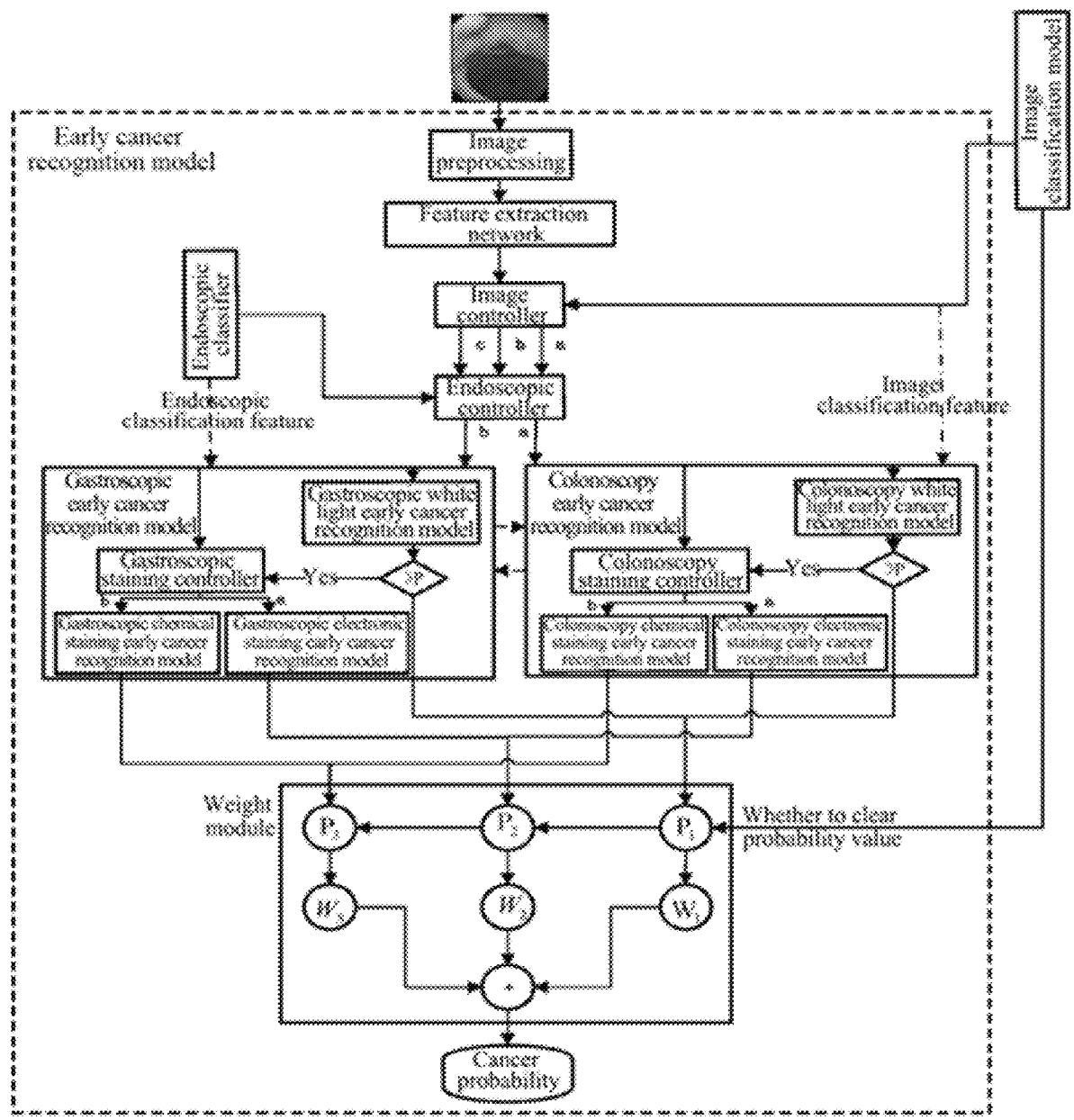
FIG. 1 is an overall block diagram of an inspection and diagnosis assistance system for early digestive tract cancer according to an embodiment of the present application.

In an embodiment of the present application, an inspection and diagnosis assistance system for early digestive tract cancer is provided, and the overall block diagram of the system is shown in FIG. 1. The inspection system includes: a feature extraction network, an image classification model, an endoscopic classifier and an early cancer recognition model. The feature extraction network is configured to extract a preliminary feature from an endoscopic image according to the neural network model; the image classification model is configured to perform secondary extraction on the preliminary features, obtain image classification features, and classify the input image modality; the endoscopic classifier is configured to perform a further feature extraction on the preliminary features obtained by the feature extraction network, and obtain endoscopic classification features; the early cancer recognition model is configured to stitch the input preliminary features, endoscopic classification features, image modality features and image classification features to obtain a probability of early cancer lesion in the white light image, electronic staining image or chemical staining image of corresponding parts, or obtain corresponding rinsing prompts or position recognition prompts.

Further, the system further includes an endoscopic controller, wherein the endoscopic controller is configured to select and enable a gastroscopic or colonoscopy early cancer recognition model according to the preliminary feature and the endoscopic classification feature.

In an embodiment, the feature extraction network may be connected to the image classification model, the endoscopic classifier and the image controller to provide the preliminary features for the image classification model, the endoscopic classifier and the image controller, respectively.

In an embodiment, the system further includes an image preprocessing module, configured to label and correspondingly standardize the endoscopic images. The endoscopic image is one of a white light image, an electronic staining image and a chemical staining image of an upper digestive tract or colonoscopy.

In an embodiment, the early cancer recognition model includes gastroscopic early cancer recognition models and colonoscopy early cancer recognition models; the gastroscopic early cancer recognition models include a gastroscopic white light early cancer recognition model, a gastroscopic electronic staining early cancer recognition model, and a gastroscopic chemical staining early cancer recognition model; the colonoscopy early cancer recognition model includes a colonoscopy white light early cancer recognition model, a colonoscopy electronic staining early cancer recognition model, and a colonoscopy chemical staining early cancer recognition model.

The system further includes a weight module, configured to weight the probability of early cancer lesions of the white light image, electronic staining image or chemical staining image of corresponding parts in an activated early cancer recognition model, and update the probability of early cancer lesions corresponding to the white light image, electronic staining image or chemical staining image of the corresponding parts.

In an embodiment, the image classification model is configured to classify input image modalities, and obtain image modality features of three modalities of white light image, electronic staining image or chemical staining image; the image classification model is further configured to provide control signals for an image controller, control signals for the weight module, and image classification features for the gastroscopic early cancer recognition model and the colonoscopy early cancer recognition model.

In an embodiment, the endoscopic classifier is configured to determine whether an input image is a gastroscopic image or a colonoscopy image, and to provide a control signal to an endoscopic controller and to provide an endoscopic classification feature for a gastroscopic early cancer recognition model and a colonoscopy early cancer recognition model.

The image controller is configured to receive the preliminary features of the feature extraction network, with three output ports a, b and c corresponding to the white light feature output, the electronic staining feature output, and the chemical staining feature output, respectively. Further, the classification result of the image classification model corresponds to the three output ports of the image controller, and only one output port of the image controller is activated to output at one time.

The endoscopic controller is configured to receive the corresponding three outputs from the image controller, obtain the corresponding colonoscopy image features and the upper digestive tract image features, and send the colonoscopy image features and the upper digestive tract image features to the colonoscopy early cancer recognition model and the gastroscopic early cancer recognition model, respectively. The colonoscopy early cancer recognition model is connected to a colonoscopy position classifier, and the gastroscopic early cancer recognition model is connected to a gastroscopic position classifier.

The endoscopic controller is further configured to receive control signals provided by the endoscopic classifier, and enabling an output port to activate the output to the colonoscopy early cancer recognition model and the gastroscopic early cancer recognition model.

The gastroscopic early cancer recognition model is configured to stitch the input gastroscopic features and input the features to a corresponding recognition model. The input gastroscopic image features include preliminary features of the feature extraction network, image classification features, endoscopic classification features, and gastroscopic position features.

The gastroscopic early cancer recognition model includes a gastroscopic white light early cancer recognition model, a gastroscopic electronic staining early cancer recognition model, and a gastroscopic chemical staining early cancer recognition model.

Further, the working mechanism of the gastroscopic early cancer recognition model is as follows: according to the endoscopic screening of clinicians, when the first output result of the image classification model is a white light image, the white light feature channel a is then firstly activated, and then the stitched gastroscopic features are firstly input into the gastroscopic white light early cancer recognition model. When it is determined that the probability of a cancer lesion in the image is greater than P (the value of P can be preset to be ranged from 1% to 10%) under white light, the physician is prompted to perform the staining operation, and the output of the gastroscopic staining controller is activated. The stained image features are input into the gastroscopic early cancer recognition model, and the features will enter the corresponding staining recognition model under the control of gastroscopic staining.

The colonoscopy early cancer recognition model is configured to stitch the input colonoscopy image features and input the features to a corresponding recognition model. The input colonoscopy image features include preliminary features of the feature extraction network, image classification features, endoscopic classification features, and colonoscopy position features.

The colonoscopy early cancer recognition models include colon white light recognition model, colon electronic staining recognition model and colon chemical staining recognition model.

The working mechanism of the colonoscopy early cancer recognition model is the same as that of the gastroscopic early cancer recognition model, in which the stitched colonoscopy image features are firstly input into the colonoscopy white light recognition model. When it is determined that the probability of the presence of cancer lesions in the image is greater than P under white light, the physician is prompted to perform the staining operation for a further determination, and the output of the colonoscopy staining controller is activated; then the other two staining recognition models are activated.

The gastroscopic early cancer recognition model and colonoscopy early cancer recognition model have a total of three outputs, namely $P_1$, $P_2$, and $P_3$, which correspond to the probability of the early cancer lesions in the current position in the white light image, electronic staining image, and chemical staining image, respectively.

In an embodiment, the weight module is configured to weight the results of the three connected recognition models to obtain prediction results with higher accuracy. The values of $P_1$, $P_2$, and $P_3$ in the weight module are continuously updated, and newly input values from recognition models will replace the original values, and are kept until a new input probability value is to be updated. An output from the image classification model is used as the control signal input of the weight module, and when the image classification model detects a white light image input, the values of $P_1$, $P_2$, and $P_3$ will be reset to zero. The output of the weight module is a result of the combined action of the white light recognition model, the electronic staining recognition model, and the chemical staining recognition model.

In an embodiment, all endoscopic image can be classified into three categories, including a white light image, an electronic staining image, and a chemical staining image. In terms of object, all images can be classified into two categories, including a gastroscopic image and a colonoscopy image. In terms of result state, all images can be classified into two categories, including presence and absence of a cancer lesion.

The image preprocessing module is configured to perform image cropping, image scaling, image standardization and image normalization. The image resolution of the original gastrointestinal endoscopy is 1920×1080, whereas only a middle area having tissue is useful, and the surrounding border needs to be manually cropped. The cropped image is scaled down to the dimension of the input network, i.e. 528×528.

The image standardization includes calculating an average map and a standard deviation map of the entire gastrointestinal endoscopy image database. The calculation method is as follows:

$$\text{mean} = \frac{1}{N}\sum_{i=1}^{N} X_i;$$

$$std = \sqrt{\frac{1}{N}\sum_{i=1}^{N}(Xi - \text{mean})^2};$$

$X_i$ is an image matrix of (528,528,3), N is the number of images in the database. Each image $X_j$ input to the network needs to be standardized as follows:

$$X_j = (X_j - \text{mean})/std$$

The image normalization is to transform the pixel value of $X_j$ into a value between 0 and 1. During training, a data augmentation operation can be performed on the image database, including image brightness and contrast transformation, image scaling transformation, image rotation transformation, image mirror transformation and local distortion transformation.

The preprocessing of prediction part also includes image cropping, image scaling, image standardization and image normalization.

The feature extraction network is mainly used to initially extract features from the input image to prepare for the subsequent classification and recognition models. Specifically, the feature extraction network may also use a network such as VGG-Net, Res-Net, SE-Net, NAS-Net, and the like.

Figure 2:
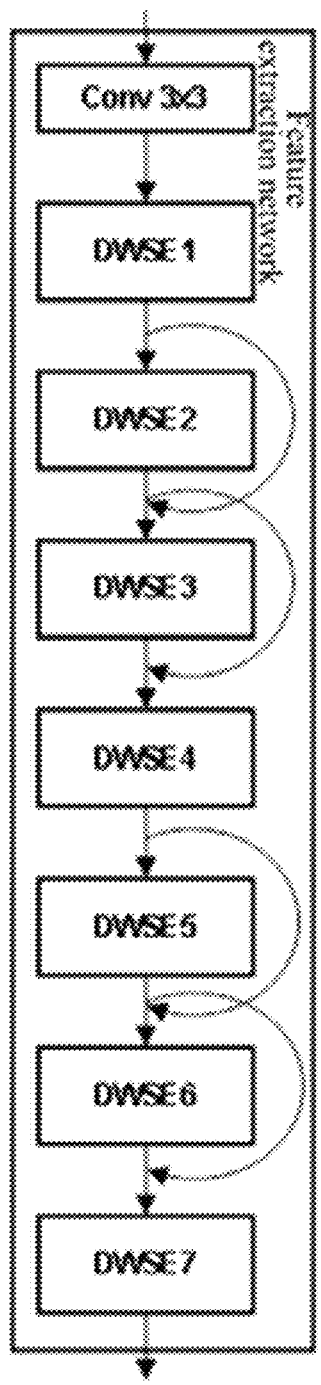
FIG. 2 is a schematic structural diagram of a feature extraction network according to an embodiment of the present application.

In an embodiment, the feature extraction network includes one ordinary convolutional layer and seven DWSE modules, as shown in FIG. 2, a short connection is added at both ends of certain DWSE modules. The feature network image input is (Batch, 3, 528, 528), and the output feature vector is (Batch, 512, 132, 132), where Batch is the size of network batch.

Figure 3:
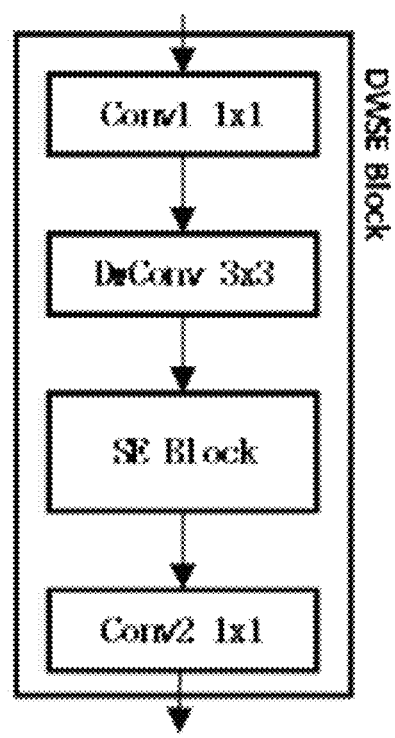
FIG. 3 is a schematic structural diagram of a DWSE module of a feature extraction network according to an embodiment of the present application.

FIG. 3 shows the structure of the DWSE module, which consists of two convolutional layers Conv1 and Conv2 both with a kernel of 1×1, a depthwise separable convolutional layer DwConv and a SE module in SE-Net. Each layer of convolution in the feature extraction network is followed by a BN layer and an ELU activation layer.

In an embodiment, after the image classification model performs a further feature extraction on the preliminary feature in the feature extraction network, image classification features are obtained and a classification task of the input image modalities (white light images, electronic staining images, and chemical staining images) is completed. The results of the modal classification are used to control the output of the image controller and the storage of the probability value of the weight module.

The endoscopic classifier is also configured to further perform feature extraction on the preliminary features from the feature extraction network to obtain endoscopic classification features and complete the classification task of classifying input images into gastroscopic or colonoscopy images. Further, the output of the endoscopic controller is controlled using the classification results of the endoscopic classifier.

The early gastroscopic cancer recognition model is configured to input the stitched features into the corresponding recognition models according to the preliminary features of the feature extraction network, the features of the image classification model, the features of the endoscopic classifier and the features of the gastroscopic position classifier, as well as based on the control of the image controller and the gastroscopic staining controller.

Whether the gastroscopic early cancer recognition model is activated is controlled by the endoscopic controller. When the input image is a gastroscopic image, the endoscopic classifier controls the endoscopic controller to activate the early gastroscopic cancer recognition model.

As shown in FIG. 1, according to the operation procedure of the clinical endoscopist, a gastroscopic image should firstly be a white light image, and the stitched white light image features should be input into the gastroscopic white light early cancer recognition model. When the recognition model predicts that the probability of the presence of a cancer lesion in the image is greater than P, the other two early gastroscopic cancer recognition models are activated, and the endoscopist is prompted to perform staining operations. What is further prompted is the existence probability of the cancerous area in the image, and the probability is just a prediction result from the gastroscopic white light image recognition model.

After the endoscopist performs the staining (electronic staining or chemical staining) operation, a corresponding gastroscopic staining recognition model works, and the recognition model also outputs a predicted probability value. In this case, the predicted probability of cancerous area in the prompt information is a weighted result of the output probabilities of the gastroscopic white light recognition model and the staining recognition model (electronic staining recognition model or chemical staining recognition model or both).

The colonoscopy early cancer recognition model has the same principle as the gastroscopic early cancer recognition model, wherein whether the gastroscopic or colonoscopy early cancer recognition models is activated is controlled by the endoscopic controller. When the input image is a colonoscopy image, the endoscopic classifier controls the endoscopic controller to input the feature extraction network features into the colonoscopy recognition model. At this point, the colonoscopy recognition model starts to work, and the gastroscopic early cancer recognition model is in a waiting state.

The weight module is configured to weight and output the results of the three image recognition models (white light, electronic staining, and chemical staining recognition models) in an activated recognition models (the gastroscopic early cancer recognition model or the colonoscopy early cancer recognition model) to obtain prediction results with higher accuracy. The calculation method is as follows:

$$P_{out}=W_1P_1+W_2P_2+W_3P_3.$$

wherein $P_{out}$ is a final probability of determining whether a cancerous area exists in the image, $P_1$, $P_2$, and $P_3$ are the probabilities of cancer lesions in the images recognized by the three activated recognition models, and $W_1$, $W_2$, and $W_3$ are the weight parameters of the weight modules.

When the white light recognition model is activated, the value of the output $P_1$ of the recognition model is stored in the weight module. When the white light recognition model is continuously activated, the stored $P_1$ will be continuously updated, and the same is true for the other two recognition models. When the staining recognition model is activated, the predicted probability of the white light recognition model is determined based on $P_1$ stored in the weight module, and the probability values from the other two recognition models after activation are also stored in the weight module. After the diagnosis of the cancerous area in a position is completed, the field of view of a probe is switched to another position, and the input image changes to a white light image again. In this case, with the help of the image classifier (i.e., when the network detects that the input image has changed from a staining image to a white light image), the weight module will clear the values of $P_1$, $P_2$, and $P_3$, and the value of $P_1$ will be updated to represent the probability of the presence of a cancerous lesion in the current white light image.

Figure 4:
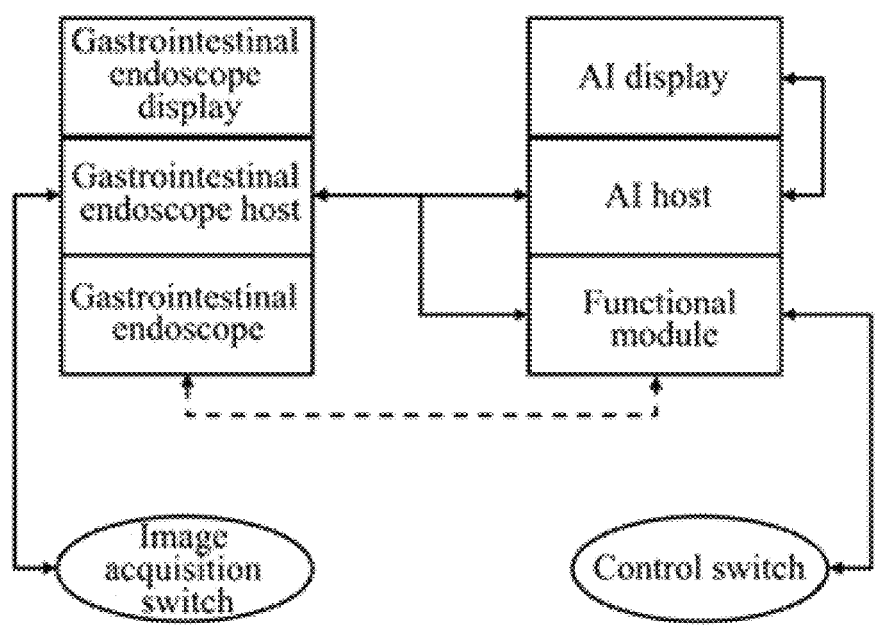
FIG. 4 is a schematic structural diagram of an inspection and diagnosis assistance device for early digestive tract cancer according to an embodiment of the present application.

In an embodiment, provided is an inspection and diagnosis assistance device for early digestive tract cancer. As shown in FIG. 4, the inspection and diagnosis assistance device for early digestive tract cancer includes an AI display, an AI processor, a functional module and a control switch. The functional modules are rinsing and staining operation modules. Conventional digestive endoscopes connected to the inspection and diagnosis assistance device include a gastrointestinal endoscope display, a gastrointestinal endoscope and a gastrointestinal endoscope host.

The AI display and the AI processor, as well as the AI processor and the gastrointestinal endoscope host, are connected to each other by video lines. The AI processor and the functional modules are connected to each other by electrical signal lines. The functional module and the gastrointestinal endoscope are connected to each other through a rinsing pipeline and a staining pipeline. The functional module and the control switch are connected through an air pressure pipe of the air pressure switch.

Provided that an endoscopist operates a gastroscope or colonoscope and looks at the AI display. When it is prompted on the display that rinsing is required through the analysis of the AI processor, the endoscopist stamps down on the control switch, such that the functional module enables a rinsing solution with a constant temperature of 37 degrees Celsius and having the functions of removing foam and mucus to rinse and clean a target area, and then releases the control switch to end rinsing. During this operation, the AI processor automatically records the relevant information about rinsing prompts and rinsing responses for quality control inspection.

If analysis is performed by the AI processor, mucosal staining is prompted by the display, the endoscopist presses the rinsing/staining conversion button and the rinsing solution selection button on the AI processor, and stamps down on the control switch, such that the functional module enables the mucosal staining solution to spray and stain the mucosa of the target area at a constant speed and uniformity, and then the endoscopist releases the control switch to end staining. During this operation, the AI processor automatically records relevant information about staining prompts and staining responses for quality control inspection.

When the esophagus is stained with compound iodine solution, the endoscopist only needs to press the staining solution selection button of the AI processor and select the compound iodine staining solution neutralizer (5% sodium thiosulfate solution), and stamps down on the control switch, such that the functional module sprays and neutralizes the mucosa of the target area at a constant speed and uniformity to prevent further stimulation of the digestive tract by the excess compound iodine solution. And then the endoscopist releases the control switch to end spraying.

Similarly, when other staining is performed in the same manner as mentioned above, the endoscopist only needs to press the rinsing/staining conversion button, and then stamps down on the control switch, such that the functional module will rinse and clean the excess staining solution in the target mucosa staining area, and then the endoscopist releases the control switch to end.

When an early cancer prompt without staining the mucosa (white light endoscopy) is displayed based on the AI technology, the endoscopist only needs to adjust the staining mode in the AI host of the device to the desired staining solution, and then stamps down on the control switch, the functional module will spray and stain the mucosa of the target area at a constant speed and uniformity (which is to perform a biopsy positioning), and then release the control switch to end the spraying and staining. Finally, the endoscopist takes out the staining spray tube, and then inserts the biopsy forceps for biopsy according to the situation.

When it is prompted an early cancer under chromoendoscopy, the endoscopist takes out the staining spray tube and inserts the biopsy forceps for biopsy according to the situation. Except for the biopsy which requires the assistance of a nurse, other procedures can be performed by the endoscopist alone.

In the general case as mentioned above, the rinsing tube is connected to a jaw or an auxiliary water supply port of the gastrointestinal endoscope. In case of a colonoscopy and insufficient bowel preparation of the examinee (at this time, rinsing is prompted on the display through AI technology), the ordinary rinsing pipeline can be replaced with an integrated rinsing and suction pipeline which can be connected to a suction port with the suction button on the colonoscope being replaced with a wireless button unique to the unit. After the rinsing/cleaning mode button on the AI processor is switched to an integrated rinsing and suction mode, the intestinal mucosa with insufficient intestinal preparation can be rinsed and cleaned. Because the bowel preparation is insufficient, ordinary rinsing and cleaning may easily cause blockage of the suction channel of the gastrointestinal endoscope.

Figure 5:
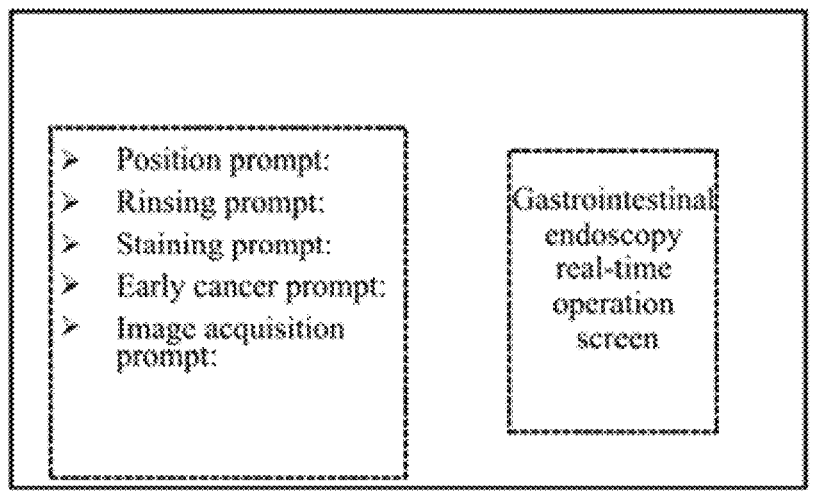
FIG. 5 is a schematic diagram of a display interface of an inspection and diagnosis assistance device for early digestive tract cancer according to an embodiment of the present application.

FIG. 5 shows the layout of the AI display of the device. As shown in FIG. 5, the real-time operation screen of the gastrointestinal endoscope is the same as that of the gastrointestinal endoscope, unless the indicated block diagram is annotated by AI. A position prompt, a rinsing prompt, a staining prompt, an early cancer prompt, and an image acquisition statistic are disposed on the left side of the display.

Figure 7:
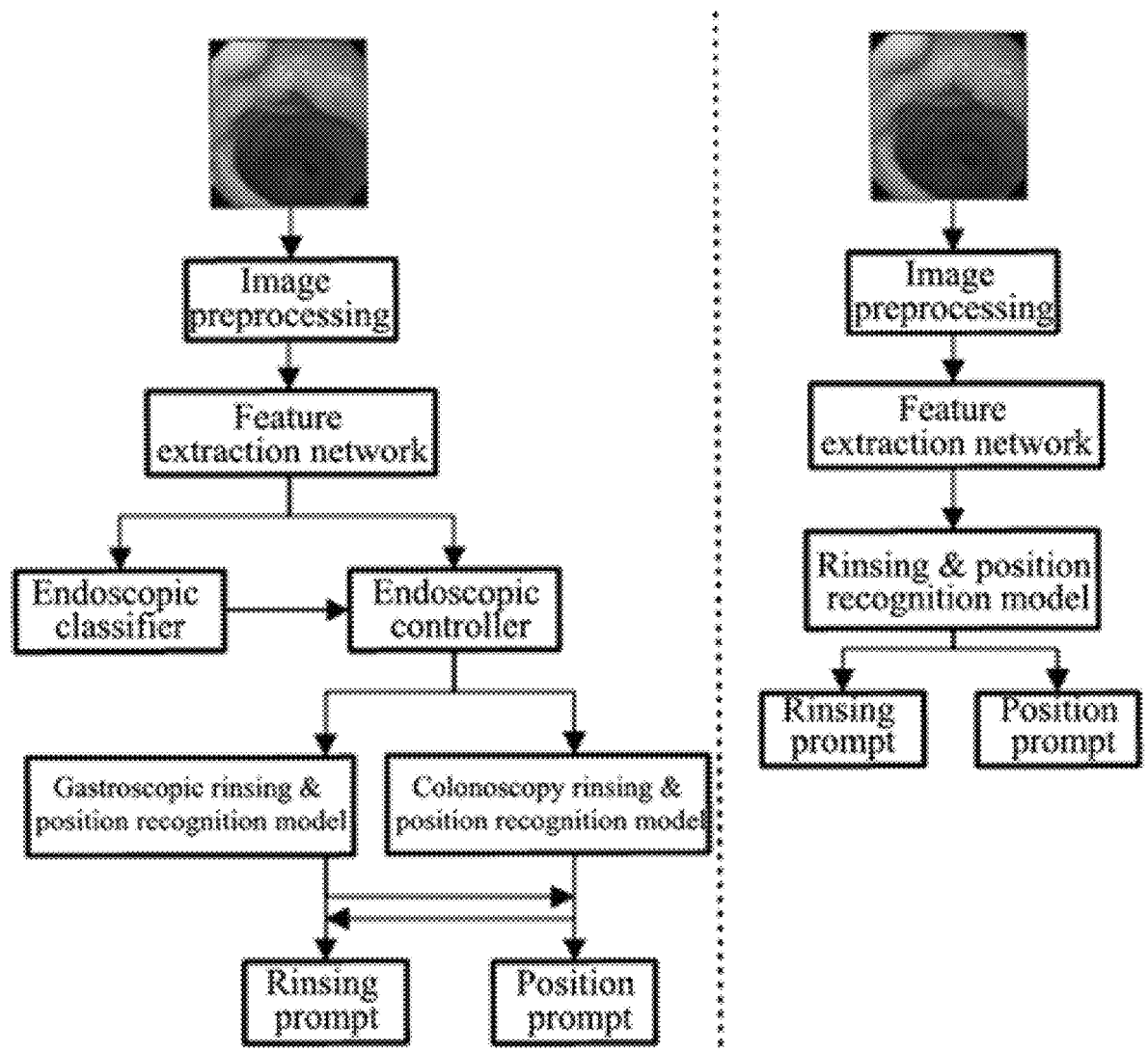
FIG. 7 is a flowchart showing operation an inspection and diagnosis assistance device for early digestive tract cancer according to an embodiment of the present application.

In an embodiment, FIG. 7 is a flowchart of the processing function of the AI processor, which shows both the left-displayed and right-displayed solutions for analysis and processing.

In the solution shown on the left, two different models for gastroscope and colonoscopy are used, and the operations of two different rinsing position models are controlled by one endoscopic classification model. The solution mainly includes image preprocessing, feature extraction network, endoscope classifier, endoscopic controller, gastroscope rinsing & position recognition model, and colonoscopy irrigation & position recognition model. The image preprocessing module is used to improve the training accuracy and generalization ability of the model, which mainly includes a preprocessing during model training and a preprocessing during prediction. In the preprocessing of the training part, model training is performed on a large amount of endoscopic data, all endoscopic data need to be manually labeled, and the labeling includes labeling a position and labeling for rinsing.

The position labeling is applicable to the upper and lower digestive tract, and the positions of the upper digestive tract include oropharynx, esophagus, cardia, fundus, gastric body, gastric angle, gastric antrum, pylorus, duodenal bulb, and descending duodenum; the positions of the lower digestive tract include ileocecal (including ileocecal valve and appendix recess), ascending colon, hepatic flexure, transverse colon, splenic flexure, descending colon, sigmoid colon, and rectum.

The grading criteria for visual field clarity of the upper digestive tract under endoscopy are as follows: Grade A: no foam, no mucus, clear visual field; Grade B: a small amount of mucous foam, relatively clear visual field; Grade C: scattered mucous foam, affected visual field; grade D: a large number of mucous foam, or reflux of bile or blood, unclear visual field. When the clarity of the visual field is in grade A or grade B, it represents that no rinsing is required, and when the clarity of the visual field is in grade C or D, it represents that rinsing is required to obtain an image.

The grading criteria for visual field clarity of the lower digestive tract under endoscopy are as follows: Grade 1: no residual feces and liquid in the intestinal cavity; Grade 2: a small amount of fecal water is in the intestinal cavity, and the whole intestinal mucosa is clearly visible; Grade 3: a small amount of feces are in the intestinal cavity, and most of the intestinal mucosa is clearly visible; Grade 4: more feces are in the intestinal cavity, and the observation of intestinal mucosa are significantly affected. When the clarity of the visual field is in grade 1 or grade 2, it represents that no rinsing is required; and when the clarity of the visual field is in grade 3 or 4, it represents that rinsing is required to obtain an image.

Figure 6:
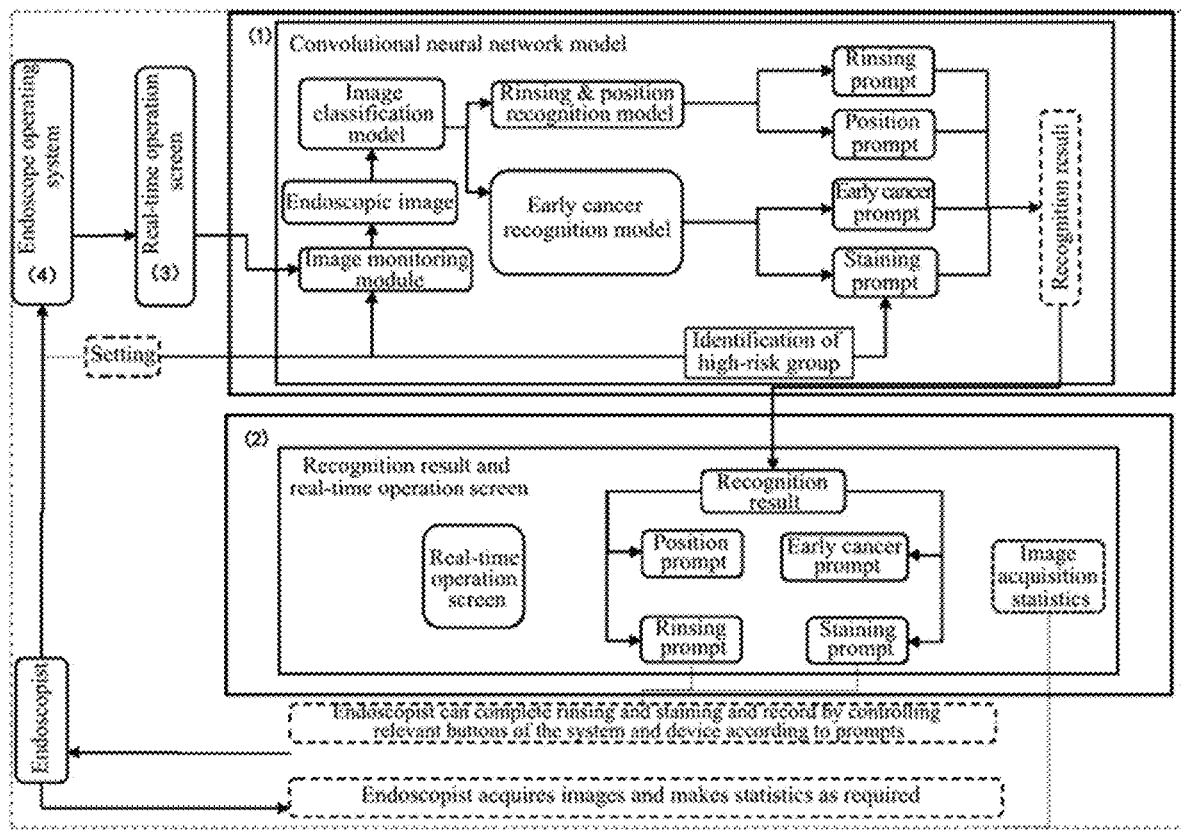
FIG. 6 is a schematic diagram of an operation method of an inspection and diagnosis assistance system for early digestive tract cancer according to an embodiment of the present application.

As shown in FIG. 6, the AI processor includes a feature extraction network, an image classification model, a rinsing position recognition model and an early cancer recognition model. The feature extraction network is used to perform preliminary feature extraction on the endoscopic images sent by the gastrointestinal endoscope host according to the neural network model. The image classification model is used to perform secondary extraction of the preliminary features, obtain image classification features, and classify the input image modalities. The rinsing position recognition model is used to receive the preliminary features of the feature extraction network, and obtain the position information of each part of the upper and lower digestive tract based on the neural network to discriminate and confirm the rinsing information. The early cancer recognition model is used to stitch the input preliminary features and image classification features to obtain the probability of early cancer lesions in the white light image, electronic staining image or chemical staining image of the corresponding parts.

The rinsing position recognition model includes a gastroscopic rinsing position recognition model and a colonoscopy rinsing position recognition model. The input of the rinsing position recognition model is the preliminary feature of the feature extraction network, and the output thereof is the discrimination of position information (i.e., each part of the upper and lower digestive tract), and the discrimination of rinsing information (i.e., whether rinsing is needed). The features in the image are extracted through a neural network framework (such as VGG-16, VGG-19, and ResNEt), and the model is divided into two branches, each of which is composed of different convolutional layers, fully connected layers and softmax layers, so as to classify the rinsing information and position information.

The system also includes an endoscopic classifier and an endoscopic controller, the endoscopic classifier is used to further perform feature extraction on the preliminary features obtained by the feature extraction network to obtain endoscopic classification features and classify gastroscopic or colonoscopy images. The endoscopic controller selects and activates the gastroscopic or colonoscopy early cancer recognition model, and the rinsing position recognition model according to the preliminary features and endoscopic classification features.

In an embodiment, the feature extraction network can be connected to the image classification model, endoscopic classifier, and image controller to provide preliminary features for the image classification model, endoscopic classifier, and image controller, respectively.

In an embodiment, the system further includes an image preprocessing module, and the image preprocessing module is used for labeling and corresponding standardization processing of the endoscopic image. The endoscopic image may be one of white light image, electronic staining image, and chemical staining image of the upper digestive tract or colonoscopy.

In an embodiment, the early cancer recognition model includes a gastroscopic early cancer recognition model and a colonoscopy early cancer recognition model. The gastroscopic early cancer recognition models include a gastroscopic white light early cancer recognition model, a gastroscopic electronic staining early cancer recognition model, and a gastroscopic chemical staining early cancer recognition model. The colonoscopy early cancer recognition models include a colonoscopy white light early cancer recognition model, a colonoscopy electronic staining early cancer recognition model, and a colonoscopy chemical staining early cancer recognition model.

The system further includes a weight module, used for weighting the results of the corresponding image recognition model in the activated early cancer recognition model, and updating the probability of early cancer lesions in the white light image, electronic staining image, or chemical staining image of the corresponding parts.

In an embodiment, the image classification model is used to classify the input image modalities, and obtain image data of modalities of white light image, electronic staining image, or chemical staining image. The image classification model is further used to provide control signals for the image controller, control signals for the weight module, and image classification features for the gastroscopic early cancer recognition model and the colonoscopy early cancer recognition model.

In an embodiment, the endoscopic classifier is used to discriminate whether an input image is a gastroscopic image or a colonoscopy image, and the endoscopic classifier is used to provide a control signal for an endoscopic controller and to provide endoscopic classification features for a gastroscopic early cancer recognition model and a colonoscopy early cancer recognition model.

The image controller is used to receive the preliminary features of the feature extraction network, corresponding to three output ports a, b and c, which correspond to white light feature output, electronic staining feature output, and chemical staining feature output, respectively. Further, the classification result of the image classification model corresponds to the three output ports of the image controller, and only one output port of the image controller is activated to output at one time.

The endoscopic controller is used to receive three outputs from the corresponding image controllers, obtain the corresponding colonoscopy image features and the upper digestive tract image features, and send the colonoscopy image features and the upper digestive tract image features to the colonoscopy early cancer recognition model and the gastroscopic early cancer recognition model. The colonoscopy early cancer recognition model is also connected to the colonoscopy position classifier, and the gastroscopic early cancer recognition model is also connected to the gastroscopic position classifier.

The early gastroscopic cancer recognition model is used to stitch the input gastroscopic features, and input the features to the corresponding recognition model. The input gastroscopic image features include preliminary features of the feature extraction network, image classification features, endoscopic classification features, and gastroscopic position features.

The gastroscopic early cancer recognition model includes a gastroscopic white light early cancer recognition model, a gastroscopic electronic staining early cancer recognition model, and a gastroscopic chemical staining early cancer recognition model.

Further, the working mechanism of the gastroscopic early cancer recognition model is as follows: when the first output result of the image classification model is a white light image based on a clinician's endoscopic screening, then a white light feature channel a is activated firstly, and the stitched gastroscopic features are firstly input into the gastroscopic white light early cancer recognition model. When it is determined that the probability of cancer lesion in the image is greater than P (the value of P can be preset to be ranged from 1% to 10%) under white light, the clinician is prompted to perform the staining operation, and the output of the gastroscopic staining controller is activated. The stained image features are input into the gastroscopic early cancer recognition model, and the features will enter the corresponding staining recognition model under the control of gastroscopic staining.

The colonoscopy early cancer recognition model is used to stitch the input colonoscopy image features and input the features to the corresponding recognition model. The input colonoscopy image features include preliminary features of the feature extraction network, image classification features, endoscopic classification features, and colonoscopy position features.

The colonoscopy early cancer recognition models include a colon white light recognition model, a colon electronic staining recognition model and a colon chemical staining recognition model.

The working mechanism of the colonoscopy early cancer recognition model is the same as that of the gastroscopic early cancer recognition model, in which the stitched colonoscopy image features are firstly input into the colonoscopy white light recognition model. When it is determined that the probability of cancer lesions in the image is greater than P under white light, the physician is prompted to perform a staining operation for a further determination, and the output of the gastroscopic staining controller is activated; then the other two staining recognition models are activated.

The gastroscopic early cancer recognition model and the colonoscopy early cancer recognition model have a total of three outputs, namely $P_1$, $P_2$ and $P_3$, which correspond to the probability of the presence of early cancer lesions under the current position in the white light image, electronic staining image, and chemical staining image, respectively.

As shown in FIG. 1, according to the operation procedure of the clinical endoscopist, the gastroscopic image should first be a white light image, and the stitched white light image features should be input into the gastroscopic white light early cancer recognition model. When the probability of the presence of cancer lesions in the image predicted by the recognition model is greater than P, the other two early gastroscopic cancer recognition models are activated, and the endoscopist is prompted to perform the staining operation, and the probability of the presence of cancerous areas in the image is prompted. The probability is a prediction result only by the gastroscopic white light image recognition model.

When the endoscopist performs the staining (electronic staining or chemical staining) operation, the corresponding gastroscopic staining recognition model starts to work, and the recognition model also outputs a predicted probability value. In this case, the predicted cancerous area probability in the prompt information is the weighted result of the output probabilities of the gastroscopic white light recognition model and the staining recognition model (electronic staining recognition model or chemical staining recognition model or both).

The principle of the colonoscopy early cancer recognition model is the same as that of the gastroscopic early cancer recognition model, in which whether the gastroscopic or colonoscopy early cancer recognition model is activated is controlled by the endoscopic controller. When the input image is a colonoscopy image, the endoscopic classifier controls the endoscopic controller to input the features from the feature extraction network into the colonoscopy recognition model. At this time, the colonoscopy recognition model starts to work, and the gastroscopic early cancer recognition model is in a waiting state.

The weight module is used to weight and output the results of the three image recognition models (white light, electronic staining, and chemical staining recognition models) in the activated recognition models (the gastroscopic early cancer recognition model or the colonoscopy recognition model) to obtain prediction results with higher accuracy.

When the white light recognition model is activated, the value of the output $P_1$ of the recognition model is stored in the weight module. When the white light recognition model is continuously activated, the stored $P_1$ will be continuously updated, and the same is true for the other two recognition models. When the staining recognition model is activated, the predicted probability of the white light recognition model is determined based on $P_1$ stored in the weight module, and the probability values by the other two recognition models after activation are also stored in the weight module. After the diagnosis of the cancerous area in a position is completed, the field of view of a probe is switched to another position, and the input image changes to a white light image again. In this case, with the help of the image classifier (i.e., when the network detects that the input image has changed from a staining image to a white light image), the weight module will clear the values of $P_1$, $P_2$, and $P_3$, and the value of $P_1$ will be updated to represent the probability of the presence of a cancerous lesion in the current white light image. In the solution shown on the right, the generalization ability of the rinsing position recognition model is enhanced, a deeper general network is used to extract features, and the gastroscope and colonoscope are put together for rinsing position recognition.

The prompt information of the system in the present application mainly includes rinsing prompt, position prompt, early cancer prompt, and staining prompt. The logical relationship between the prompt information is as follows: during the inspection of normal people, the prompt information of a certain part under white light condition has both rinsing and staining prompts, and the AI display only outputs the rinsing prompt. After the endoscopist performs the rinsing operation, provided that the rinsing and staining prompts still coexist, both prompts will be displayed on the AI display.

Staining prompts are determined by both the early cancer recognition model and an endoscopist-identified criteria for high-risk groups. Provided that a case is defined by the endoscopist as belonging to the high-risk group of cancer, the system will automatically prompt a mucosal staining in an inspection of each part of the esophagus and colonoscopy (the prompt is not affected by the early cancer recognition model). When gastric and duodenal inspections are performed, prompts are output according to the early cancer recognition model in the same manner as for the normal people.

The statistics of the image acquisition displayed in the real-time operation screen are mainly based on the records of the number of images required by the nation and the number of images taken by physicians during actual treatment.

The system and device of the present application are mainly intended to assist endoscopists in discovering early-stage cancer lesions that are easily overlooked during endoscopy of parts including esophagus, stomach, duodenum, and colon, so as to reduce the missed detection rate of early-stage cancers.

Those of ordinary skill in the art can understand that all or part of the steps for implementing the above-mentioned method embodiments may be completed by hardware related to program instructions, the program may be stored in a computer-readable storage medium, and when the program is executed, the steps of the above-mentioned method embodiments are executed. The aforementioned storage medium includes: ROM, RAM, magnetic disk, compact disk and other media that can store program codes.

The above-mentioned electronic device embodiments are only illustrative, the units described as separate components may or may not be physically separated, and the components shown as units may or may not be physical units, namely they may be either located in one place, or distributed to multiple network elements. Some or all of the modules may be selected according to actual needs to achieve the objectives of the solutions in the embodiments. Those of ordinary skill in the art can understand and implement them without creative effort.

From the description of the above-mentioned embodiments, those skilled in the art can clearly understand that each embodiment can be implemented by means of software plus a necessary general hardware platform, and certainly can also be implemented by hardware. Based on such understanding, the essential parts of the above technical solutions or the parts that make contributions to the prior art can be embodied in the form of computer software products. The computer software products can be stored in a computer-readable storage medium, such as ROM/RAM, magnetic disk, compact disk, and include several instructions for causing a computer device (which can be a personal computer, a server, a network device and the like) to execute the methods described in various embodiments or portions of embodiments.

Finally, the methods introduced in the present application are only preferred embodiments, and are not intended to limit the protection scope of the present application. Any modification, equivalent substitution and improvement made within the sprits and principles of the present application shall be included within the protection scope of the present application.

We claim:

1. A deep learning based inspection and diagnosis assistance system for early digestive tract cancer, comprising a feature extraction network, an image classification model, an endoscopic classifier and an early cancer recognition model,
   wherein the feature extraction network is configured to extract a preliminary feature from an endoscopic image according to a neural network model;
   the image classification model is configured to perform an extraction on the preliminary feature, acquire an image modality feature and acquire an image classification feature corresponding to a gastroscopic or colonoscopy image;
   the endoscopic classifier is configured to extract the preliminary feature, and obtain an endoscope classification feature; and
   the early cancer recognition model is configured to stitch the preliminary feature, the endoscope classification feature, the image modality feature and the image classification feature, and obtain a probability of early cancer lesion in a white light image, an electronic staining image or a chemical staining image of a corresponding part or obtain a washing prompt or a position recognition prompt of the corresponding part.

2. The system of claim 1, further comprising an endoscopic controller, configured to select and enable a gastroscopic or colonoscopy early cancer recognition model based on the preliminary feature and the endoscope classification feature.

3. The system of claim 1, further comprising an image preprocessing module, configured to label and standardize the endoscopic image, wherein the endoscopic image is one of a white light image, an electronic staining image and a chemical staining image of an upper digestive tract or colonoscopy.

4. The system of claim 1, wherein the early cancer recognition model comprises a gastroscopic early cancer recognition model and a colonoscopy early cancer recognition model;
   the gastroscopic early cancer recognition model comprises a gastroscopic white light early cancer recognition model, a gastroscopic electronic staining early cancer recognition model, and a gastroscopic chemical staining early cancer recognition model; and
   the colonoscopy early cancer recognition model comprises a colonoscopy white light early cancer recognition model, a colonoscopy electronic staining early cancer recognition model, and a colonoscopy chemical staining early cancer recognition model.

5. The system of claim 4, further comprising a weight module, which is configured to weight the probability of the early cancer lesion in the white light image, the electronic staining image or the chemical staining image of a corresponding part in an activated early cancer recognition model, and update the probability of the early cancer lesion corresponding to the white light image, electronic staining image or chemical staining image of the corresponding part.

6. The system of claim 5, wherein the image classification model is configured to classify an input image modality, and obtain the image modality feature of the white light image, the electronic staining image or the chemical staining image; and the image classification model is further configured to provide a control signal for an image controller, a control signal for the weight module, and the image classification feature for the gastroscopic early cancer recognition model and the colonoscopy early cancer recognition model.

7. The system of claim 1, wherein the endoscopic classifier is configured to determine whether an input image is a gastroscopic image or a colonoscopy image, and the endoscopic classifier is configured to provide a control signal to an endoscopic controller and provide an endoscopic classification feature for a gastroscopic early cancer recognition model and a colonoscopy early cancer recognition model.

8. The system of claim 7, wherein the endoscopic controller is configured to receive the control signal provided by the endoscopic classifier, and to enable an output port to activate the colonoscopy early cancer recognition model and the gastroscopic early cancer recognition model.

9. The system of claim 7, wherein the gastroscopic early cancer recognition model is configured to input, based on control of an image controller and a gastroscopic staining controller, stitched features into a corresponding recognition model according to a stitching of the preliminary feature, the image classification feature, the endoscopic classification feature and a position feature, and obtain the probability of the early cancer lesion in the white light image, the electronic staining image or the chemical staining image of the corresponding part.

10. A deep learning based inspection and diagnosis assistance device for early digestive tract cancer, comprising an AI display, an AI processor, a functional module and a control switch, the functional module being a rinsing and staining operation module, wherein the AI processor is connected with the functional module through an electrical signal line, and is configured to control, according to a judgment result of the AI processor, the functional module based on a signal of the control switch;

wherein the AI processor comprises a feature extraction network, an image classification model, an endoscopic classifier and an early cancer recognition model, wherein the feature extraction network is configured to extract a preliminary feature from an endoscopic image sent by a gastrointestinal endoscope host according to a neural network model;

wherein the image classification model is configured to perform an extraction on the preliminary feature to obtain an image classification feature, and classify an input image modality, wherein the early cancer recognition model is configured to stitch the input preliminary features and image classification feature to obtain a probability of early cancer lesions in a white light image, an electronic staining image or a chemical staining image of a corresponding part;

the functional module and a gastrointestinal endoscope are connected with each other through a rinsing pipeline and a staining pipeline; and the functional module and the control switch are connected with each other through a line of a foot switch.

11. The device of claim 10, wherein the AI processor further comprises a rinsing position recognition model comprising a gastroscopic rinsing position recognition model and a colonoscopy rinsing position recognition model, and the rinsing position recognition model is configured to recognize, according to the preliminary feature of the feature extraction network, position information of various parts of an upper digestive tract and a lower digestive tract and determine the rinsing information of a corresponding position.

12. The device of claim 10, wherein the AI processor further comprises a rinsing position recognition model configured to receive the preliminary feature from the feature extraction network, and obtain position information of various parts of an upper digestive tract and a lower digestive tract based on the neural network model to determine rinsing information.

13. The device of claim 12, wherein the AI display is configured to prompt rinsing and staining operations according to a result of the AI processor;

the control switch is configured to enable the functional module to rinse or stain a target area, wherein the AI processor is further configured to record information about rinsing and staining prompts and rinsing and staining responses.

14. The device of claim 12, wherein the AI processor further comprises an image preprocessing module, wherein the image preprocessing module is configured to label and standardize endoscopic images; and the endoscopic image is one of a white light image, an electronic staining image and a chemical staining image of the upper digestive tract or a colonoscopy.

15. The device of claim 12, wherein the early cancer recognition model comprises a gastroscopic early cancer recognition model and a colonoscopy early cancer recognition model;

the gastroscopic early cancer recognition model comprises a gastroscopic white light early cancer recognition model, a gastroscopic electronic staining early cancer recognition model, and a gastroscopic chemical staining early cancer recognition model; and the colonoscopy early cancer recognition model comprises a colonoscopy white light early cancer recognition model, a colonoscopy electronic staining early cancer recognition model, and a colonoscopy chemical staining early cancer recognition model.

16. The device of claim 12, wherein the endoscopic classifier is configured to determine whether an input image is a gastroscopic image or a colonoscopy image, and the endoscopic classifier is configured to provide a control signal to an endoscopic controller and provide an endoscopic classification feature for a gastroscopic early cancer recognition model and a colonoscopy early cancer recognition model.

17. The device of claim 12, wherein the rinsing position recognition model is configured to input, based on an endoscopic controller, stitched features into a corresponding recognition model according to a stitching of preliminary features of the feature extraction network, an image classification feature, and an endoscopic classification feature, and obtain position information of various parts of the upper digestive tract and lower digestive tract, and determine the rinsing information.

18. The device of claim 12, wherein the rinsing position recognition model is further configured to input stitched features into the recognition model according to the preliminary feature of the feature extraction network and the image classification feature, obtain the position information of various parts of the upper digestive tract and lower digestive tract, and determine the rinsing information.

* * * * *